Figure 1:
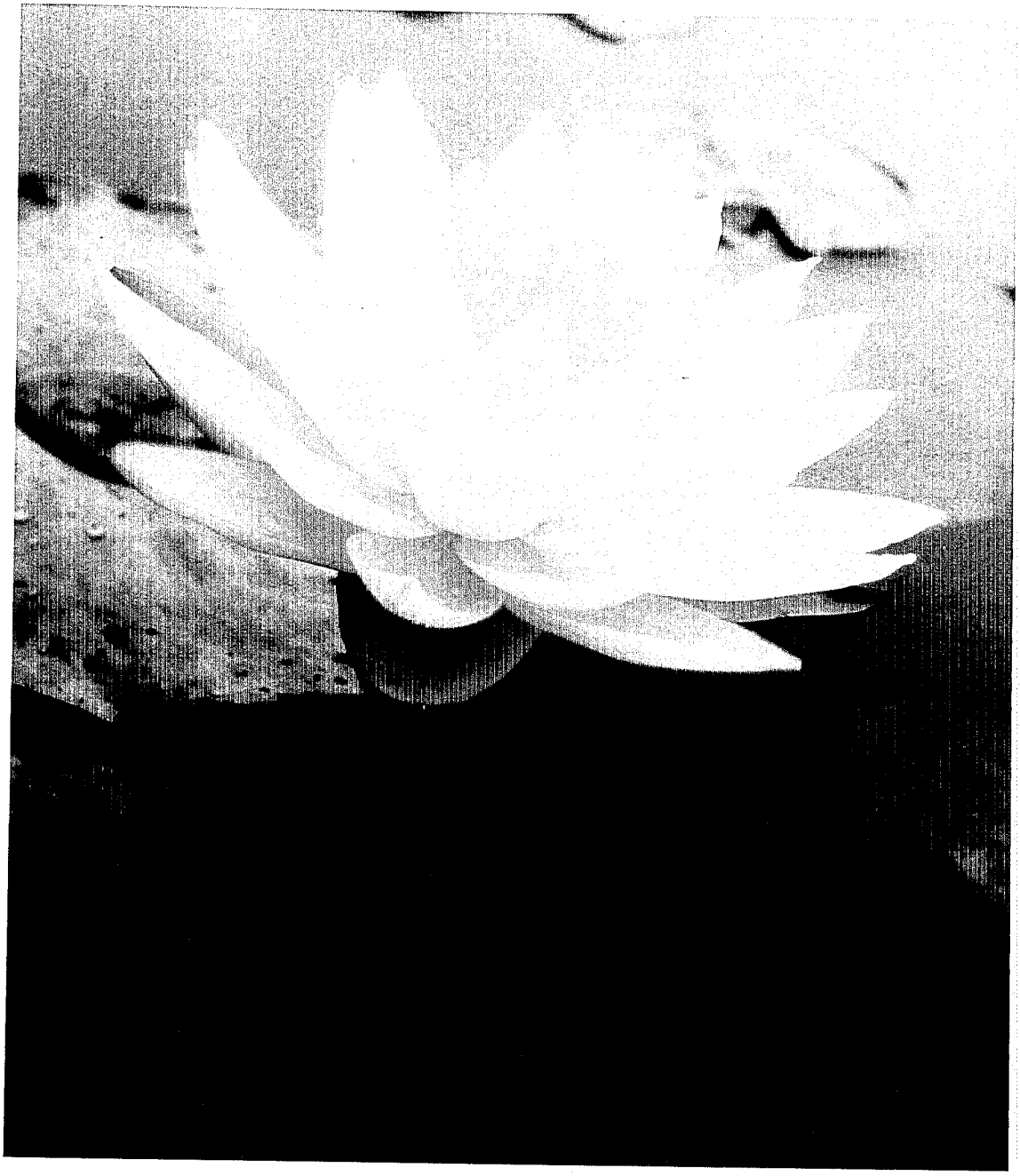
Figure 2:
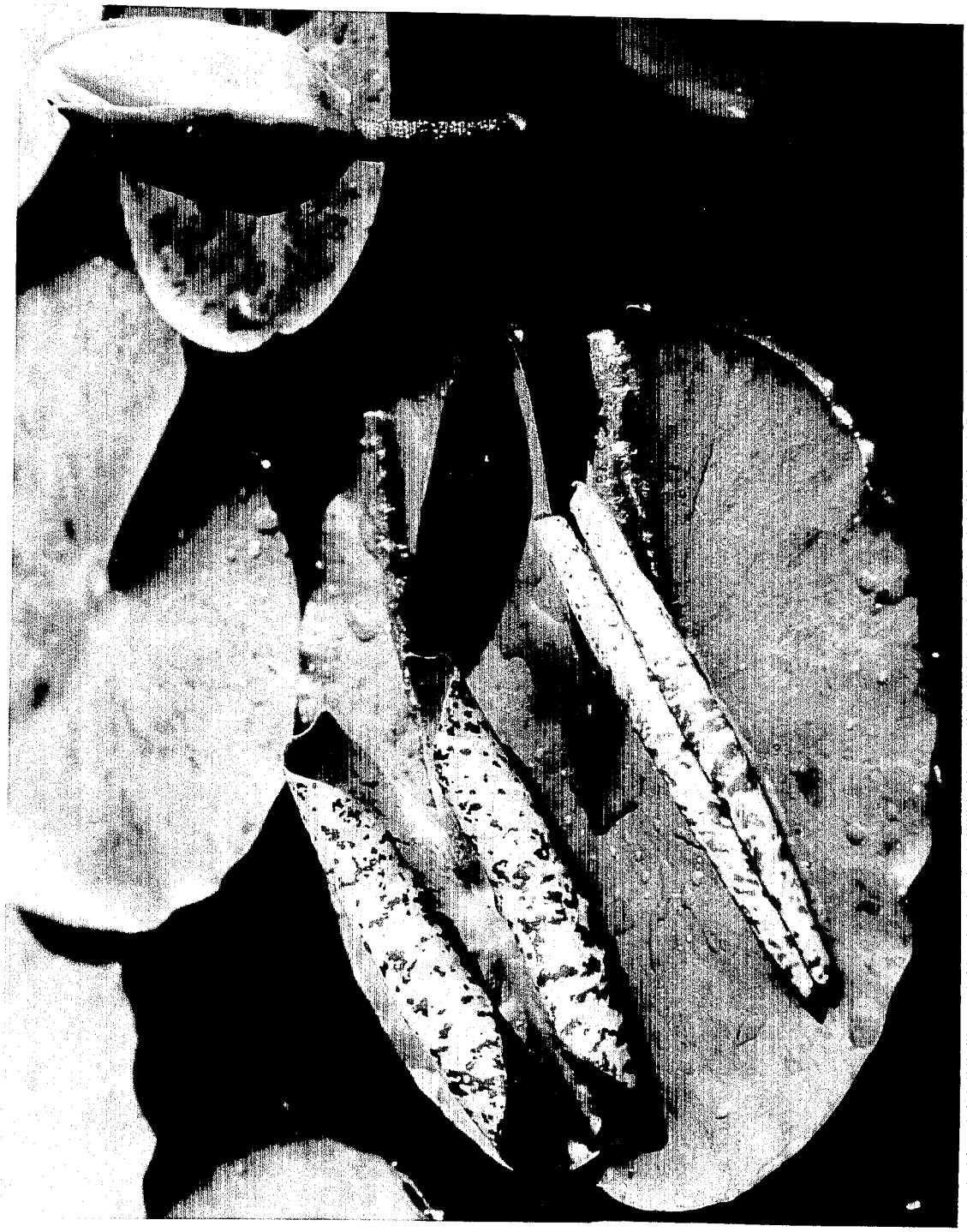
Figure 3:
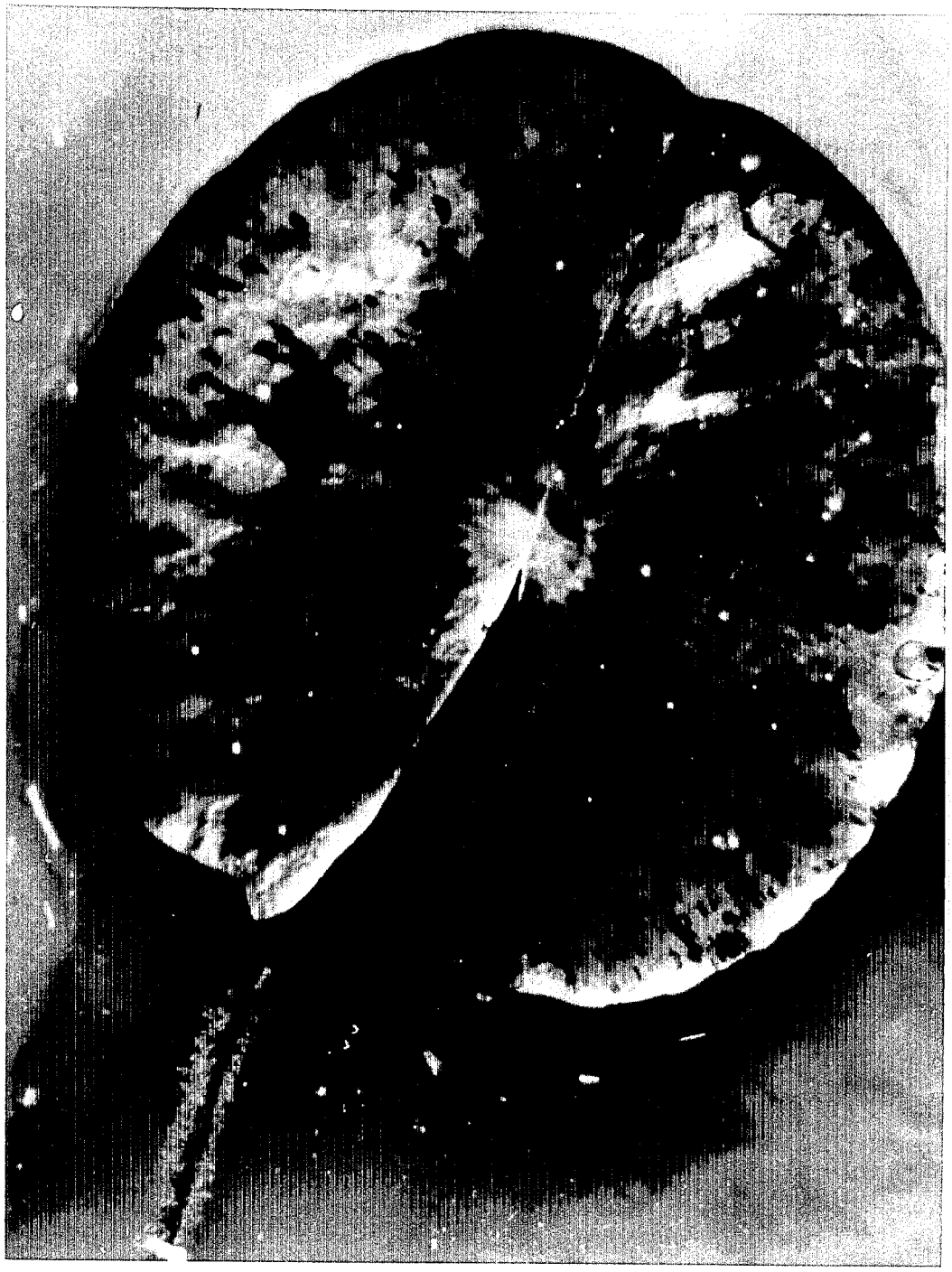
Figure 4:
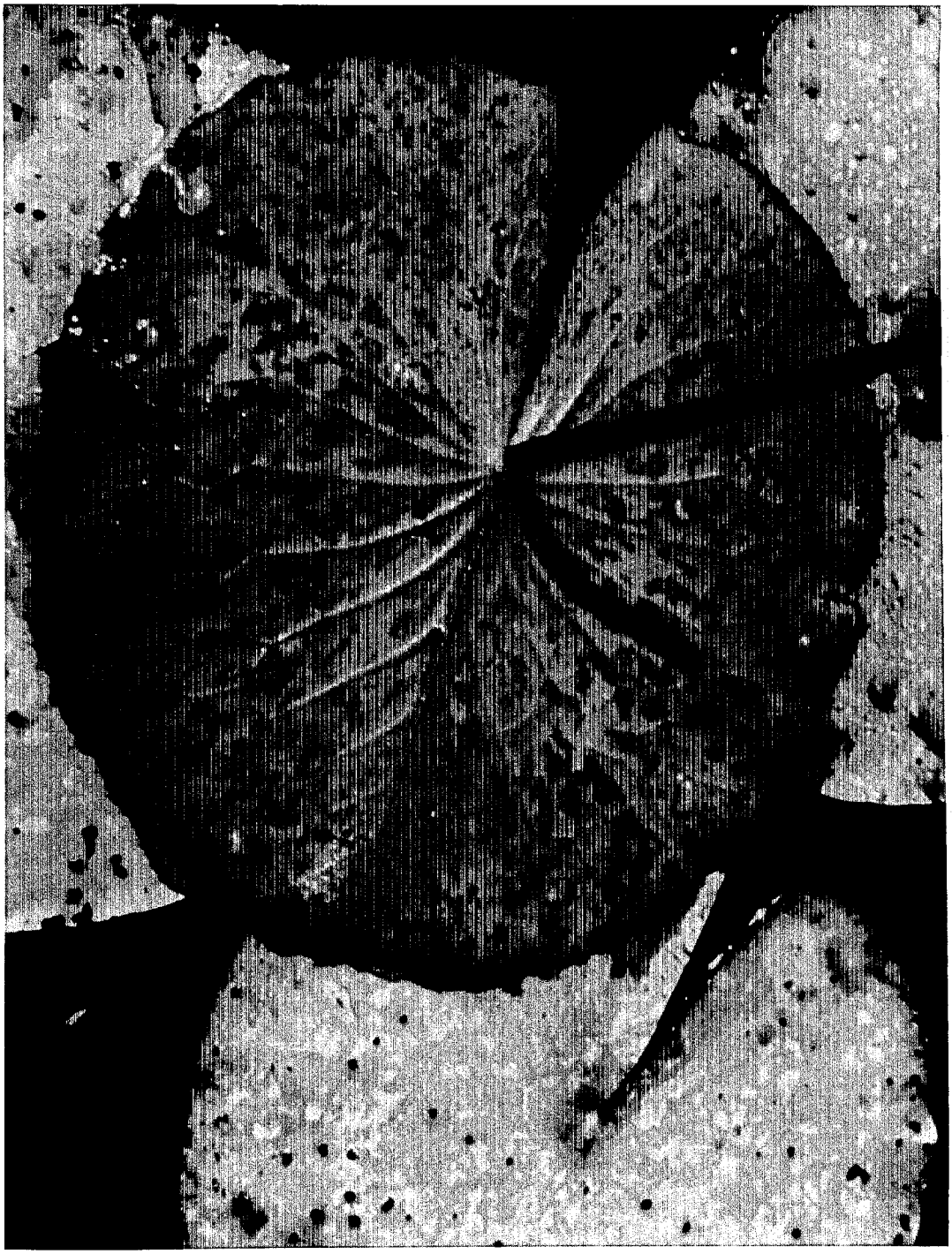
Figure 5:
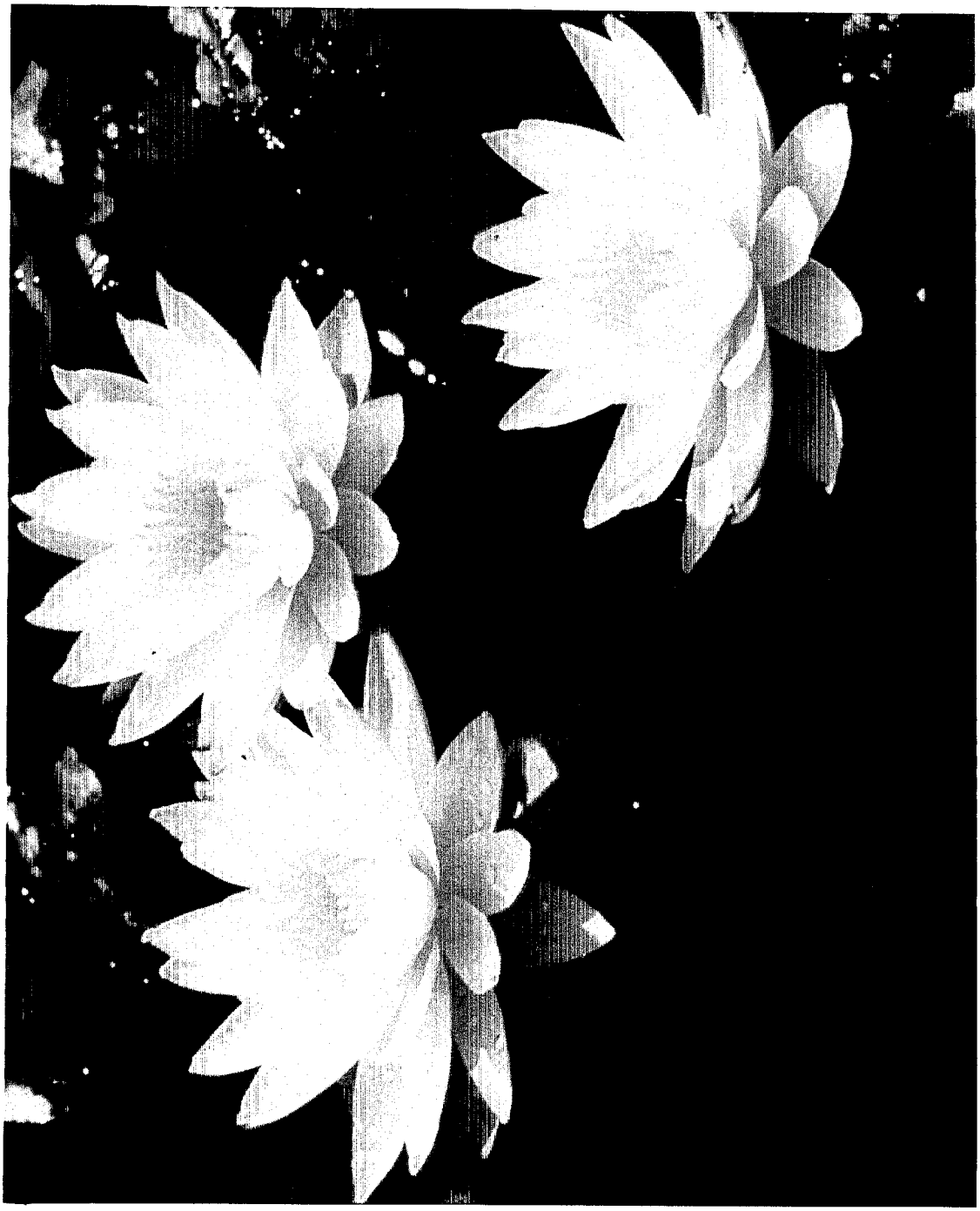

US00PP09676P

United States Patent [19]

Slocum

[11] Patent Number: Plant 9,676

[45] Date of Patent: Oct. 29, 1996

[54] WATER LILY, PLANT NAME: 'PEACHES AND CREAM'

[76] Inventor: Perry D. Slocum, 1831 Leatherman Gap Rd., Franklin, N.C. 28734

[21] Appl. No.: 605,555

[22] Filed: Feb. 20, 1996

[51] Int. Cl.[6] ..... A01H 5/00

[52] U.S. Cl. ..... Plt./87.16

[58] Field of Search ..... Plt./87.16

[56] References Cited

U.S. PATENT DOCUMENTS

P.P. 5,799 11/1986 Slocum ..... Plt./87.16

*Primary Examiner*—James R. Feyrer

[57] ABSTRACT

A novel day-blooming water lily having stellate-shaped flowers borne approximately 75–130 mm above the water with large leaves having a green upper surface and a red underside.

5 Drawing Sheets

The present invention relates to a new and distinct variety of water lily named Peaches and Cream of the decorative class which was originated by Perry D. Slocum by crossing a Nymphaea, variety: 'Texas Dawn' with a Nymphaea, variety: 'Perry's Viviparous Pink'.

The primary objective of this breeding was to produce a new and improved water lily variety having a colorful pink and yellow flower which was hardy with the flowers extending substantially above the leaves. This objective was achieved along with other desirable improvements as evidenced by the unique combination of characteristics which are outstanding in the new variety and which distinguish it from all other water lily varieties by its:

(1) flowers of substantially pink outer petals with yellow inner petals;

(2) round leaves having convolutions along the edges which are green on top with purple flecks on young leaves and red underneath with reddish-purple flecks, and (3) flower petals curled inwardly with a delightful fragrance.

Asexual reproduction of the new variety which was performed at Franklin, N.C., by tuber division shows that the foregoing characteristics and distinctions come true to form and are established and transmitted through succeeding propagations.

The accompanying photographs show in FIGS. 1–5 typical specimens of the flower (FIGS. 1 and 5) stem (FIG. 2), bud (FIG. 2) and leaves (FIGS. 3 and 4) of the new water lily variety in different stages of development and as depicted in color as nearly true as is reasonably possible to make the same in color photographs of this character.

The following is a detailed description of the new variety, with color terminology in accordance with: Royal Horticultural Society Color Chart, published by Royal Horticultural Society, London, in association with the Flower Council of Holland, Leiden.

Parentage: Seedling.

*Seed parent.*—Nymphaea, 'Texas Dawn'.

*Pollen parent.*—Nymphaea, 'Perry's Viviparous Pink'.

p0 Classification: Decorative.

Height: Flowers are approximately 75–130 mm above water with 190–255 mm diameter leaves with flowers approximately 150–205 mm in diameter and approximately 75–130 mm above the leaves.

Location where grown and observed: Outdoors in water pools in Franklin, N.C. throughout the year.

Cold resistance: Hardy perennial.

Blooming period: In Franklin, N.C. climatic area, blooming begins in late April and continues through September.

LEAVES

Upper side, at first: Olive green #148C, heavily mottled with purple #79C blotches which practically disappear after a few weeks. The #148C color changes to #147D color after a few weeks.

Underside: Bright red #181C with purple blotches #184B. Leaf is nearly round, being slightly wider than long, sinus is open. Usually 6–7 mm projections are present at tips of lobes next to sinus.

FLOWER

Bud: Outside of sepals have #145C color to #146D color variation. Sepals open up #38B to #38C on inside of flower.

*When petals first divide (FIG. 5).*—Uppermost petals are #6B. Middle petals #13D–29D with the bottom petals being #38C.

Bloom:

*Size.*—150–205 mm in diameter.

*Stem.*—Stiff, strong #184B.

*Form.*—First day petals are cup-shaped, second and third days flowers are fully opened. (See FIGS. 4 and 5).

*Petalage.*—Usually about 32–37 in number.

*Sepals.*—4 in number.

*Stamen.*—80–94 in number.

*Anther.*—80–94 in number.

*Color.*—Center of flower—Center of pistils #15B at the pistil edge, #15B with anthers #15B and stamens #15B. Outer petals are between #38C–38D and #38D–13D with the inner petals being #6B.

Petals:

*Texture.*—Smooth.

Fragrance: Very delightfully fragrant.

PLANT

Form: All branching of the plant is done underwater.

Growth: Medium about 75–130 mm above water.

Foliage:

*Size.*—190–255 mm diameter leaves.

*Quantity.*—Plentiful with 1–2 meter spread.

*Color.*—#147D on mature leaves.

*Texture.*—Convoluted edges with smooth leaves as shown in FIG. 1.

Stem color: #184B, Pubescens quite thick on stems.

I claim:

1. A new and distinct variety of water lily plant substantially as herein shown and described.

* * * * *